US006309405B1

United States Patent
Bonutti

(10) Patent No.: US 6,309,405 B1
(45) Date of Patent: *Oct. 30, 2001

(54) SUTURE ANCHOR

(76) Inventor: Peter M. Bonutti, 1303 W. Evergreen Plz., Effingham, IL (US) 62401

( * ) Notice: Subject to any disclaimer, the term of this patent is extended or adjusted under 35 U.S.C. 154(b) by 0 days.

This patent is subject to a terminal disclaimer.

(21) Appl. No.: 09/344,982

(22) Filed: Jun. 25, 1999

Related U.S. Application Data

(62) Division of application No. 08/929,628, filed on Sep. 15, 1997, now Pat. No. 5,989,282, which is a division of application No. 08/626,393, filed on Mar. 29, 1996, now Pat. No. 5,713,921.

(51) Int. Cl.[7] .................................................. A61B 17/04
(52) U.S. Cl. .............................................................. 606/232
(58) Field of Search ..................................... 606/232, 184, 606/139, 73, 72, 64, 60, 151, 74, 144, 220; 24/115, 122.6

(56) References Cited

U.S. PATENT DOCUMENTS

| | | |
|---|---|---|
| 3,596,292 * | 8/1971 | Erb et al. ........................... 623/15.11 |
| 4,890,612 | 1/1990 | Kensey . |
| 5,061,274 | 10/1991 | Kensey . |
| 5,269,809 * | 12/1993 | Hayhurst et al. ..................... 606/232 |
| 5,370,660 | 12/1994 | Weinstein et al. . |
| 5,403,348 | 4/1995 | Bonutti . |
| 5,488,958 | 2/1996 | Topel et al. . |
| 5,540,718 | 7/1996 | Bartlett . |
| 5,626,612 | 5/1997 | Bartlett . |
| 5,718,717 | 2/1998 | Bonutti . |
| 5,968,046 | 10/1999 | Reed . |
| 5,968,047 | 10/1999 | Reed . |

OTHER PUBLICATIONS

Article entitled "The Search for the Holy Grail: a Century of Anterior Cruciate Ligament Reconstruction", by R. John Naranja, Jr., MD, John Corsetti, MD, Jeffrey R. Kuhlman, MD, and Joseph S. Tory, MD, *The American Journal of Orthopedics*, Nov. 1997, pp. 743–752.

* cited by examiner

*Primary Examiner*—Henry J. Recla
*Assistant Examiner*—Vy Q. Bui
(74) *Attorney, Agent, or Firm*—Tarolli, Sundheim, Covell, Tummino & Szabo, L.L.P.

(57) ABSTRACT

An improved suture anchor is formed from body tissue. The body tissue is shaped to a desired configuration for the anchor and defines a passage through the anchor. A suture is inserted into the passage in the body tissue of the anchor. The anchor is then positioned in a patient's body with a suture extending into the passage in the anchor. The anchor may be formed of osseous body tissue, hard compact bone, dense connective body tissue, or other body tissue. The body tissue may be dried so that it absorbs fluid and expands upon being inserted into a patient's body.

59 Claims, 3 Drawing Sheets

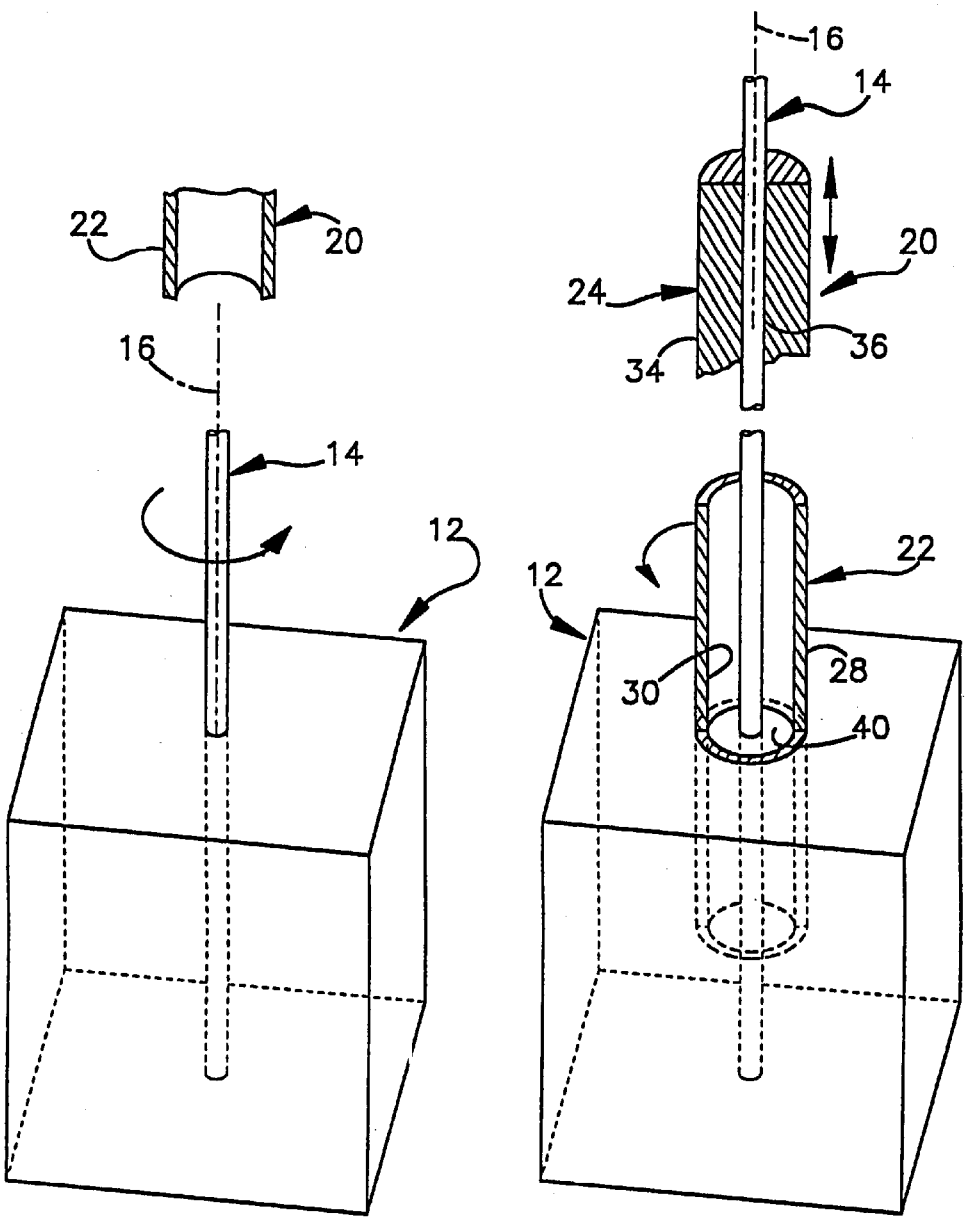
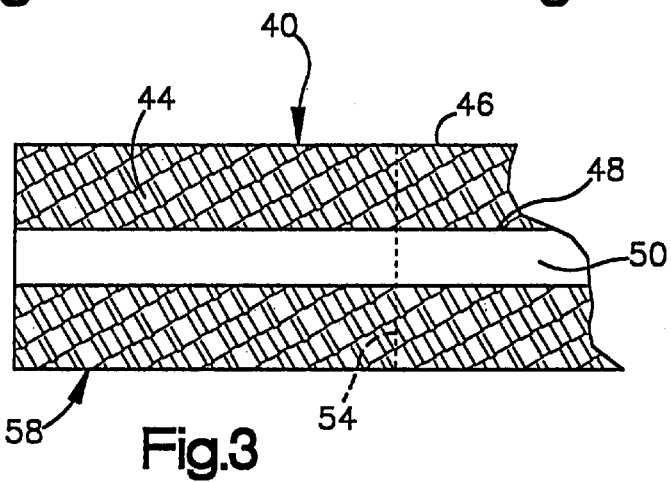
Fig.1  Fig.2  Fig.3

SUTURE ANCHOR

This application is a division of Application Ser. No. 08/929,628, filed Sep. 15, 1997, now U.S. Pat. No. 5,989,282. The aforementioned application Ser. No. 08/929,628 is itself a division of Application Ser. No. 08/626,393, filed Mar. 29, 1996, now U.S. Pat. No. 5,713,921. The benefit of the earlier filing dates of the aforementioned applications is hereby claimed.

BACKGROUND OF THE INVENTION

The present invention relates to a new and improved suture anchor and more specifically to a suture anchor which is formed of body tissue.

Anchors are commonly utilized to retain sutures in a patient's body. The anchors have previously been formed of metal, such as stainless steel or titanium. In addition, anchors have been formed of biodegradable materials. While being generally satisfactory, these known anchors have the drawback that they are material which is not body tissue and are inserted into a patient's body. It has previously been suggested to construct anchors in the manner disclosed in U.S. Pat. Nos. 5,405,359; 5,403,348; 5,203,787; 5,046,513; and 5,041,129.

SUMMARY OF THE INVENTION

The present invention relates to a new and improved suture anchor which is formed of body tissue. The body tissue is shaped to the desired configuration of the anchor. The body tissue defines a passage through the anchor. A suture is inserted into the passage in the anchor. The anchor and the suture are inserted into a patient's body.

The anchor may be formed of many different types of body tissue, including osseous body tissue, bone, or dense connective tissue. The body tissue may be dried so that when the anchor is exposed to fluid in a patient's body, the anchor absorbs the fluid and expands. The body tissue may be from the patient's body, from another human, or from a non-human animal.

BRIEF DESCRIPTION OF THE DRAWINGS

The foregoing and other features of the invention will become more apparent upon a consideration of the following description taken in connection with the accompanying drawings, wherein:

FIG. 1 is a schematic illustration depicting the manner in which a thin elongated member is inserted into body tissue;

FIG. 2 is a schematic illustration, generally similar to FIG. 1, illustrating the manner in which a cutting tool is moved axially along the thin elongated member into the body tissue;

FIG. 3 is an enlarged schematic illustration of body tissue formed with the thin elongated member and cutting tool of FIGS. 1 and 2;

DESCRIPTION OF SPECIFIC PREFERRED EMBODIMENTS OF THE INVENTION

General Description

Figure 4:
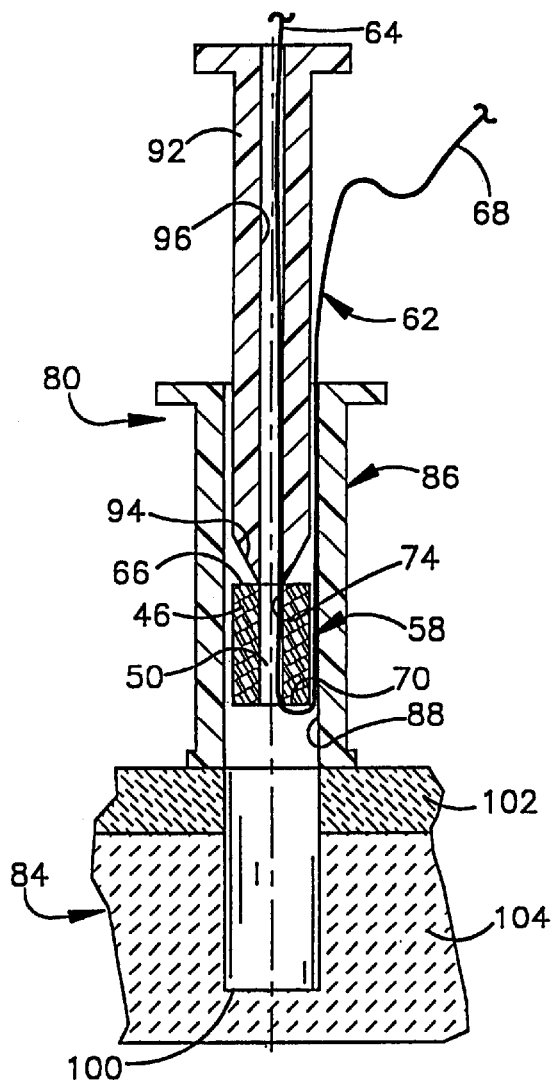
FIG. 4 is a schematic illustration depicting the manner in which an anchor formed of the body tissue of FIG. 3 is inserted into a patient's body with a suture extending into the anchor.

Suture anchors have previously been utilized to retain sutures in either hard or soft tissue in a human patient's body. The suture anchors have previously been formed of metal, biodegradable materials, and other materials which do not naturally occur in a patient's body. The insertion of materials other than body tissue into a patient's body may be objectionable.

In accordance with a feature of the present invention, sutures are retained in a patient's body by anchors formed of body tissue. In one specific embodiment of the invention, the anchor is formed of bone or osseous (bonelike) tissue. In another embodiment of the invention, the anchor is formed of dense connective body tissue. The dense connective body tissue may contain collagen. The dense connective body tissue may be cartilage, tendon or ligament. The dense connective body tissue may be interarticular fibrocartilage which previously formed a meniscus in a joint. Although it is believed that it may be preferred to use bone, osseous tissue, or dense connective tissue to form the anchor, other body tissue may be utilized if desired.

It is contemplated that the body tissue which is used to form the anchor may be dried. When an anchor formed of dried body tissue is inserted into a patient's body at a location where it is exposed to the fluids in the patient's body, the anchor absorbs the body fluid and expands. As the anchor expands, it presses against the surrounding tissue in the patient's body and becomes firmly interlocked with the surrounding tissue of the patient's body.

It is contemplated that the body tissue forming the anchor may be dried in many different known ways. Specifically, the body tissue may be dried by placing it in a press and applying pressure against the body tissue to force fluid from the body tissue. Alternatively, the body tissue may be freeze dried or dried by exposure to a relatively warm dry environment. The dried body tissue which forms the anchor may be bone, osseous tissue, dense connective tissue, or other body tissue. For example, the dried body tissue forming the anchor could be formed of dried skin or other soft tissue and be used to retain a suture in soft body tissue.

It is contemplated that the body tissue used to form the anchor may be the patient's own body tissue (autograft). It is believed that this has the advantage of minimizing the remote possibility of infecting a patient with the material of the anchor. However, the body tissue forming the anchor may be obtained from another human patient (allograft) or from a non-human animal, such as a bovine animal (xenograft).

It is contemplated that an anchor formed of body tissue in accordance with the present invention may have many different configurations. Thus, the anchor may have a polygonal configuration or a generally spherical configuration. However, it is believed that it may be preferred to form the anchor with a cylindrical configuration and with a passage to receive a portion of a suture.

When an anchor is to be formed, a thin elongated member may be inserted into body tissue. The thin elongated member is used to guide a cutting tool as it moves into the body tissue. The cutting tool forms a cylindrical outer side surface of the anchor. The thin elongated member forms a passage which extends through the anchor. Although this method of forming the anchor may be preferred, it is contemplated that other methods of forming the anchor could be utilized if desired. For example, the body tissue may be shaped with a press or molded to a desired configuration.

Anchor Formed of Bone or Osseous Body Tissue

Body tissue 12 is illustrated schematically in FIG. 1. The body tissue 12 may be disposed within a human patient's body or may be separate from the patient's body. The body tissue 12 may be the patient's own body tissue or may be body tissue from another human patient. Alternatively, the body tissue 12 may be from a non-human animal, such as a bovine animal. Although the body tissue 12 has been illustrated in FIG. 1 as having a polygonal configuration, the body tissue 12 may have any desired configuration. When the body tissue 12 is disposed within a patient's body, it is contemplated that the body tissue will have a configuration corresponding to the configuration of a naturally occurring portion of the patient's body.

The body tissue 12 may be natural or artificial bone or osseous body tissue. In the embodiment of the invention illustrated in FIG. 1, the body tissue 12 is hard compact human bone of the type which encloses soft cancellous bone. The bone forming the body tissue 12 may be a bone in the body of the human patient, for example, a portion of a femur of a patient. However, in FIG. 1, the body tissue 12 is illustrated as being spaced from the patient's body.

When a suture anchor is to be formed from the body tissue 12, a thin elongated metal member 14 is inserted into the hard compact human bone. The thin elongated member 14 may be a K-wire or similar article. The thin elongated member 14 is inserted into the hard bony body tissue 12 by rotating the thin elongated member about its longitudinal central axis 16 and pressing a leading end of the thin elongated member against the body tissue.

The leading end of the thin elongated member 14 may be pointed or may have a flat circular configuration. If desired, the leading end of the thin elongated member 14 may be provided with a cutting edge, similar to a cutting edge used on a drill. Although it is preferred to rotate the thin elongated member 14 as it is inserted into the hard compact bone 12, with other body tissue, the thin elongated member may be inserted without being rotated about its central axis.

In the illustrated embodiment of the thin elongated member 14, the thin elongated member has a cylindrical outer side surface with a diameter which corresponds to the desired diameter of a passage to be formed in a suture anchor formed of the body tissue 12. In the procedure illustrated in FIG. 1, the thin elongated member 14 is rotated about the axis 16 and pushed completely through the piece of body tissue 12. However, if desired, the thin elongated member 14 could be moved only part way through the body tissue 12. For example, when the body tissue 12 is disposed within a patient's body, it is contemplated that the thin elongated member 14 may not be inserted completely through the portion of the patient's body formed by the body tissue.

Once the thin elongated member 14 has been inserted into the body tissue 12, in the manner illustrated in FIG. 1, a rotating metal cutting tool 20 is moved axially along the thin elongated member 14 into the body tissue. The cutting tool 20 has a leading or cutting portion 22 (FIG. 2) and a trailing or guiding portion 24. The cutting portion 22 of the cutting tool 20 has a tubular cylindrical configuration. Thus, the leading or cutting portion 22 of the cutting tool 20 has a cylindrical outer side surface 28 and a cylindrical inner side surface 30. The cutting portion 22 of the cutting tool 20 has a leading end portion which may form a portion of a cone or which may have cutting teeth to promote a cutting action as the cutting tool is rotated and moved axially along the thin elongated member 14.

The trailing or guiding portion 24 of the cutting tool 20 has a cylindrical outer side surface 34. The outer side surface 34 forms a continuation of the cylindrical outer side surface 28 of the leading or cutting portion 22 of the cutting tool. In addition, the trailing or guiding portion 24 of the cutting tool 20 has a cylindrical inner side surface 36. The inner side surface 36 engages and is freely movable relative to the cylindrical outer side surface of the thin elongated member 14.

The cylindrical inner side surface 36 of the guiding portion 24 of the cutting tool 20 engages the cylindrical outer side surface of the thin elongated member 14. This enables the guiding portion 24 to maintain the leading or cutting portion 22 of the rotating cutting tool 20 in a coaxial relationship with the thin elongated member 14. Although it is preferred to rotate the cutting tool 20 as it is moved into the hard compact bone 12, with other body tissue, the cutting tool may be inserted without being rotated about its central axis 16.

After the thin elongated member 14 has been inserted into the body tissue 12, in the manner illustrated in FIG. 1, the cutting tool 20 is moved into telescopic engagement with the thin elongated member. The cutting tool 20 is rotated about the central axis 16 of the thin elongated member by an electric or pneumatic motor or similar device. As the cutting tool 20 is rotated about the longitudinal central axis 16 of the thin elongated member 14, the cutting tool is moved axially along the thin elongated member into engagement with the body tissue 12.

As the leading or cutting portion 22 of the rotating cutting tool 20 moves into engagement with the body tissue 12, the cutting portion cuts a very thin annular groove around the thin elongated member 14 in a coaxial relationship with the thin elongated member. As the cutting tool 20 moves axially into the body tissue 12, a cylindrical core 40 of body tissue is cut from the block of bone. The cylindrical core 40 of body tissue is disposed within the tubular leading end portion 22 of the cutting tool 20. Once a core 40 of a desired axially extent has been cut in the body tissue 12, the cutting tool 20 is moved upward (as viewed in FIG. 2) along the thin elongated member and out of engagement with the body tissue 12. The core 40 is then removed from the remaining body tissue 12.

The core 40 (FIG. 3) has a tubular cylindrical configuration. The cylindrical core 40 has a tubular wall 44 formed of the body tissue 12. The tubular wall 44 has a cylindrical outer side surface 46 which is coaxial with a cylindrical inner side surface 48. The cylindrical outer side surface 46 has a diameter corresponding to the desired outside diameter of a suture anchor. The cylindrical outer side surface 46 of the tubular side wall 44 was formed by and has the same diameter as the inner side surface 30 of the cutting portion 22 of the cutting tool 20.

The cylindrical inner side surface 48 of the core 40 has a diameter corresponding to the diameter of the cylindrical outer side surface of the thin elongated member 14. The cylindrical inner side surface 48 forms a passage 50 which extends axially through the cylindrical core 40. The tubular side wall 44 of the cylindrical core 40 is formed as one piece of the body tissue 12.

The core 40 has an axial extent which is greater than the desired axial extent of a suture anchor. Therefore, the core 40 is cut, along a line indicated at 54 in FIG. 3, to form a suture anchor 58 with a desired axial extent. Although the core 40 may be cut or ground to form an anchor 58 with any one of many different axially tapering or flaring configurations, such as those disclosed in U.S. Pat. No. 5,403,348, it is believed that it may be preferred to form the anchor 58 with a cylindrical configuration.

Although it is contemplated that the tubular cylindrical suture anchor 58 could be of many different sizes, it is believed that the suture anchor may preferably have a length or axial extent of between 2 and 4 millimeters. The cylindrical outer side surface 46 of the suture anchor 58 may have a diameter of between 1 and 2 millimeters. The cylindrical inner side surface 48 of the passage 50 in the suture anchor 58 may have a diameter of ½ to 1 millimeters. Of course, the suture anchor 58 could be formed with different dimensions if desired.

Since the volume of body tissue which is required to form the suture anchor 58 is relatively small, the bone which forms the suture anchor 58 can be removed from a patient's own body with minimal detrimental effect to the patient. Thus, the thin elongated member 14 may be inserted into a bone in a patient's body. The cutting tool 20 would then be used to cut the bone in the patient's body. Of course, if desired, the body tissue for the suture anchor 58 could be obtained from another source, such as another human or from a non-human animal.

Once the suture anchor 58 has been formed from the body tissue 12, a suture 62 (FIG. 4) is inserted into the passage 50 in the suture anchor 58. The suture 62 includes a portion or leg 64 which extends away from an annular end surface 66 of the anchor 58. In addition, the suture 62 has a second portion or leg 68 which extends across an annular end surface 70 of the anchor 58. The leg 68 of the suture 62 extends along the cylindrical outer side surface 46 of the anchor 58 to a location adjacent to and spaced from the leg portion 64 of the suture 62. A relatively short portion 74 of the suture 62 interconnects the leg portions 64 and 68 and is disposed in the passage 50 in the suture anchor 58.

An inserter assembly 80 is used to position the suture anchor 58 and a portion of the suture 62 in a patient's body tissue 84. The inserter assembly 80 includes a cylindrical tubular outer sleeve 86 having a central passage 88 in which the anchor 58 is disposed. The inserter 80 also includes a tubular inner sleeve 92 which is telescopically received in the outer sleeve 86. The tubular inner sleeve 92 has a bevelled leading end portion 94 which engages the trailing end surface 66 of the anchor 58.

The leg or portion 64 of the suture 62 extends through a cylindrical passage 96 in the inner sleeve 92. The leg or portion 68 of the suture 62 extends through the central passage 88 in the outer sleeve 86 along a path which extends between the inner and outer sleeves. However, if desired, one of the legs or portions 64 or 68 of the suture could be omitted. If this was done, the suture 62 could be tied off at one end of the anchor 58.

It is contemplated that the anchor 58 may be inserted into a human patient's body at may different locations. The anchor 58 may be inserted into either hard or soft tissue. In the situation illustrated schematically in FIG. 4, the anchor 58 is being inserted into bone tissue 84 in a patient's body. A recess 100 is formed in the bone tissue 84 of the human patient's body by drilling or other methods. The recess 100 extends through the hard compact outer layer 102 of the patient's bone tissue 84 into the relatively porous inner or cancellous tissue 104. The illustrated anchor 58 is formed of the same bone as the hard outer layer 102.

To insert the anchor 58 in the patient's body tissue 84, the inner sleeve 92 is moved axially downward (as viewed in FIG. 4) to apply force against the trailing annular end surface 66 of the anchor 58. Once the anchor 58 has been pushed into the recess 100 by axial movement of the inner sleeve 92 relative to the outer sleeve 86, the leg 68 of the suture 62 is tensioned to apply force against the leading annular end surface 70 of the anchor 58. At the same time, the bevelled leading end 94 of the inner sleeve 92 is pressed against the trailing end surface 66 of the anchor.

This results in the application of a counterclockwise (as viewed in FIGS. 4 and 5) torque to the anchor 58. This torque causes the anchor to pivot through the orientation shown in FIG. 5 toward the orientation shown in FIG. 6. Once the anchor has been pivoted to the orientation shown in FIG. 6, by tensioning the suture 62 and applying force against the anchor with the leading end portion 94 of the inner sleeve 92, the anchor 58 engages the hard compact outer layer 102 of the patient's bone tissue 84 to hold the anchor in the recess 100.

The suture 68 can then be used to secure body tissue 110 in place. The body tissue 110 may be soft tissue, or a ligament, or a tendon, or other body tissue. If desired, the suture 62 may be used to secure an implant or splint in place relative to the patient's body tissue 84.

Figure 5:
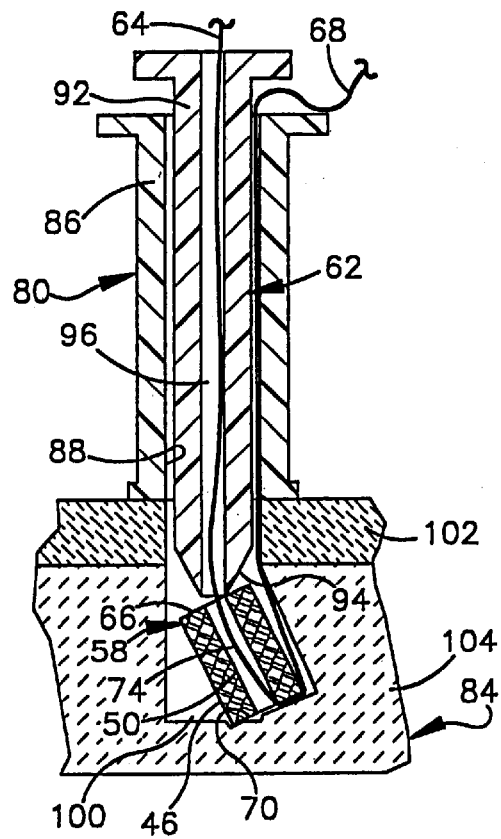
FIG. 5 is a schematic illustration depicting the manner in which the anchor of FIG. 4, formed of body tissue, is pivoted in a patient's body.
Figure 6:
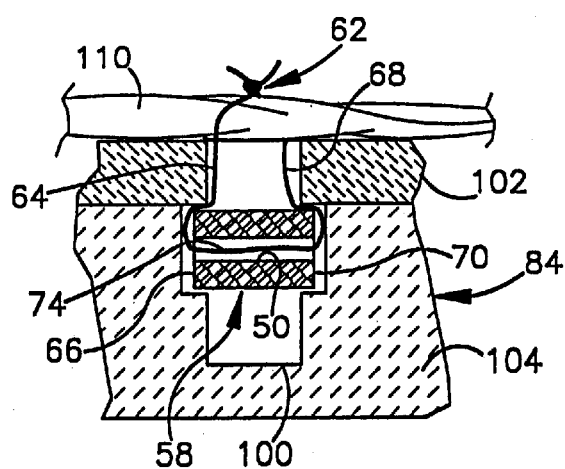
FIG. 6 is a schematic illustration depicting the manner in which the patient's body tissue is secured with a suture which extends into the anchor formed of body tissue.

One specific known inserter assembly 80 and method of inserting a suture anchor 58 into a patient's body tissue has been illustrated in FIGS. 4–6. This specific inserter assembly and the method of inserting the anchor 58 are the same as is disclosed in U.S. Pat. No. 5,403,348 issued Apr. 4, 1995 and entitled "Suture Anchor". However, it is contemplated that many different known types of inserter assemblies could be utilized to install the suture anchor with many different methods in a patient's body tissue. For example, the inserter assembly and method disclosed in U.S. Pat. No. 5,464,426 issued Nov. 7, 1995 and entitled "Method of Closing Discontinuity in Tissue" could be utilized if desired. Of course, other known apparatus and methods could also be utilized if desired.

In the embodiment of the invention illustrated in FIGS. 1–6, the anchor 58 is formed of hard compact outer bone. However, it is contemplated that the anchor 58 could be formed of osseous body tissue other than hard compact bone. The osseous body tissue could be obtained from the patient or from other sources.

Anchor Formed of Dense Connective Body Tissue

Figure 9:
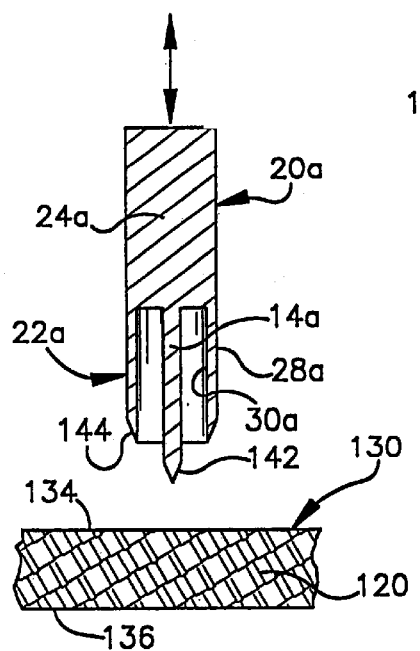
FIG. 9 is a schematic illustration depicting the manner in which a cutting tool is used to cut an anchor from the body tissue shaped with the press of FIG. 8.

In the embodiment of the invention illustrated in FIGS. 1–6, the anchor 58 is formed of osseous tissue. In the embodiment of the invention illustrated in FIGS. 7–9, an anchor is formed of dense connective body tissue. Since the embodiment of the invention illustrated in FIGS. 7–9 is generally similar to the embodiment of the invention illustrated in FIGS. 1–6, similar numerals will be utilized to identify similar components, the suffix letter "a" being associated with the components of FIGS. 7–9 to avoid confusion.

Figure 7:
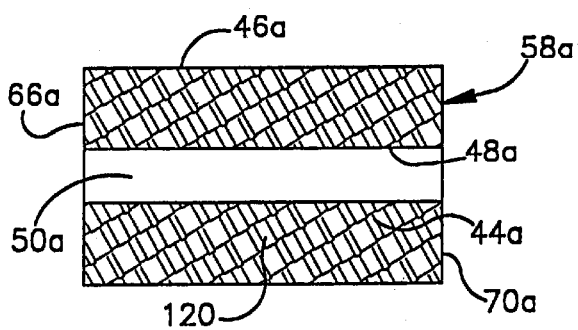
FIG. 7 is a sectional view of an anchor formed of dense connective body tissue.
Figure 8:
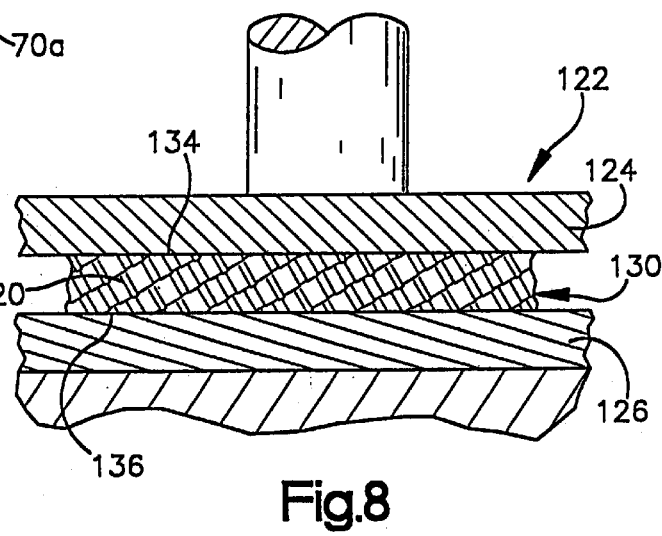
FIG. 8 is a schematic illustration depicting the manner in which dense connective body tissue is shaped in a press.

A suture anchor 58a formed of dense connective body tissue is illustrated in FIG. 7. The suture anchor 58a has the same configuration as the suture anchor 58 of FIGS. 3 and 4. The suture anchor 58a cooperates with a suture in the same manner as in which the suture anchor 58 cooperates with the suture 62 (FIGS. 4–6).

The suture anchor 58a (FIG. 7) has a cylindrical tubular side wall 44a formed of dense connective body tissue. The tubular side wall 44a has a cylindrical outer side surface 46a and a cylindrical inner side surface 48a which extend between axially opposite annular end surfaces 66a and 70a of the suture anchor 58a. The cylindrical inner side surface 48a is disposed in a coaxial relationship with the cylindrical outer side surface 46a and defines a passage 50a which extends axially through the suture anchor 58a.

Although the suture anchor 58a has a tubular cylindrical configuration, it is contemplated that the suture anchor 58a could have a different configuration if desired. For example, the suture anchor 58a could have a polygonal configuration. If desired, the suture anchor 58a could be formed with a spherical configuration. The suture anchor 58a may have an axially tapering or flaring configuration, similar to the configurations of anchors disclosed in the aforementioned U.S. Pat. No. 5,403,348.

In accordance with a feature of this embodiment of the invention, the suture anchor 58a is formed of dense connective body tissue 120. The dense connective body tissue contains collagen. It is contemplated that the dense connective body tissue 120 may be formed from ligaments or tendon. It is also contemplated that the dense connective body tissue 120 may be formed from cartilage, such as interarticular fibrocartilage which forms a meniscus in a joint. It should be understood that dense connective body tissue other than the specific examples set forth above may be utilized if desired.

The dense connective body tissue 120 forming the suture anchor 58a may be removed from a patient's own body. Alternatively, the dense connective body tissue may be obtained from a human other than the patient into which the suture anchor 58a is to be inserted. If desired, the dense connective body tissue 120 could be obtained from a non-human animal, such as a bovine animal. However, it is believed that it may be preferred to use a patient's own dense connective body tissue to form the suture anchor 58a in order to minimize any possibility of infection. If the dense connective body tissue is obtained from a source other than a patient's own body, it may be desired to sterilize the dense connective body tissue using ethylene oxide gas or other sterilizing agents.

Although the dense connective body tissue 120 could be shaped in many different ways, it is preferred to place the dense connective body tissue in a press 122 (FIG. 8). The press 122 has an upper platen 124 which presses the dense connective body tissue 120 against a lower platen 126 to form a flat sheet 130 of dense connective body tissue. The flat sheet 130 has a thickness, as measured perpendicular to parallel flat upper and lower major side surfaces 134 and 136 (FIG. 9) of the flat sheet, which is equal to the desired axial extent of the suture anchor 58a (FIG. 7). Thus, the thickness of the flat sheet 130 is equal to the distance between opposite annular end surfaces 66a and 70a (FIG. 7) of the suture anchor 58a.

A cutting tool 20a (FIG. 9) is used to cut the sheet 130 to form the suture anchor 58a. The cutting tool 130 includes a thin elongated member 14a having a cylindrical outer side surface with a diameter which corresponds to the diameter of the passage 50a in the suture anchor 58a (FIG. 7). In the illustrated embodiment of the cutting tool 20a, a leading end portion 142 of the thin elongated member 14a has a sharp conical configuration. However, if desired, the leading end portion 142 could have a flat circular configuration. Alternatively, the leading end portion 142 of the thin elongated member 14a could have a thin hollow tubular configuration.

The cutting tool 20a has a leading or cutting portion 22a. the leading or cutting portion 22a has a cylindrical outer side surface 28a and a cylindrical inner side surface 30a. The cutting portion 22a of the cutting tool 20a has a sharp leading end portion 144 which is formed as a portion of a right circular cone having a central axis which is coincident with the central axis of the cutting tool 20a and with the central axis of the thin elongated member 14a. A trailing portion 24a of the cutting tool 20a is gripped by a drive device (not shown).

When the suture anchor 58a is to be formed from the sheet 130 of dense connective body tissue 120, the drive device moves the cutting tool 20a straight downward (as viewed in FIG. 9) without rotating the cutting tool. As the cutting tool 20a moves downward, the thin elongated member 14a is inserted into and pierces the sheet 130 of dense connective body tissue 120. Immediately after the leading end portion 142 of the thin elongated member 14a enters the sheet 130 of dense connective body tissue 120, the leading end portion 144 of the cutting portion 22a engages the sheet 130 of dense connective body tissue. Continued downward (as viewed in FIG. 9) movement of the cutting tool 20a results in the cutting portion 22a of the cutting tool cutting the sheet 130 of dense connective body tissue with a cookie cutter type action.

This results in a cylindrical opening being formed in the sheet 130 and in a body of dense connective body tissue 120 being disposed in the cutting tool 20a. The body of dense connective body tissue is removed from the cutting tool 20a with a suitable ejector (not shown). The body of dense connective body tissue 120 which is ejected from the cutting tool 20a will have a configuration corresponding to the configuration of the suture anchor 58a. It should be noted that the cutting tool 20a is reciprocated with a linear cutting and return stroke and is not rotated about its central axis as is the cutting tool 20 of FIG. 2.

If desired, the cutting tool 20a and thin elongated member 14a could be rotated together about their common central axis as they are moved into the body tissue 120. This would result in the same type of cutting action as is obtained with the separate thin elongated member 14 and cutting tool 20 of FIGS. 1 and 2. However, the rotating thin elongated member 14a and cutting tool 20a would cut the body tissue simultaneously rather than sequentially as in FIGS. 1 and 2.

It should be understood that a separate thin elongated member, corresponding to the thin elongated member 14 of FIGS. 1 and 2, and a rotatable cutting tool, corresponding to the cutting tool 20 could be utilized to cut the dense connective body tissue. If desired, the dense connective body tissue could have a configuration other than the configuration of the sheet 130. Thus, a relatively large block or piece of dense connective body tissue could be provided. Alternatively, the dense connective body tissue of the anchor 58a could be obtained directly from the patient's own body with the cutting tool 20a.

For example, the thin elongated member 14 could be inserted axially into the dense connective body tissue in the manner illustrated in FIG. 1 for the body tissue 12. The thin elongated member could be inserted into the dense connective body tissue while the thin elongated member is being rotated and pressed against the dense connective body tissue in the same manner as described in conjunction with the body tissue 12 of FIG. 1. The rotating cutting tool 20 will then cut a relatively long cylindrical core of dense connective body tissue. Once the core of dense connective body tissue has been removed from the cutting tool 20 and the thin elongated member 14, the cylindrical core of dense connective body tissue would be cut to a length corresponding to the desired length of the suture anchor 58a.

It is also contemplated that a suitable press could be utilized to shape the dense connective body tissue into the cylindrical configuration of the anchor 58a. Thus, a press having a construction similar to the construction disclosed in U.S. Pat. No. 5,329,846 issued Jul. 19, 1994 and entitled "Tissue Press and System" could be utilized to form the dense connective body tissue to a cylindrical configuration. If desired, the body tissue could be shaped around a thin elongated member which is subsequently withdrawn to form the passage 50a. Alternatively, the thin elongated member could be inserted into a cylindrical piece of dense connective body tissue to form the passage 50a after the body tissue has been removed from the press or while the body tissue is still in the press.

Once the suture anchor 58a has been formed, a suture is inserted into the passage 50a and the suture anchor is inserted into the body of a patient. The suture anchor 58a may be inserted to the body of a patient using an inserter assembly having the same construction as the inserter assembly 80 of FIGS. 4 and 5. Once the suture anchor 58a has been pushed into a patient's body, the suture is tensioned and force is applied against the trailing end of the suture anchor by the inner sleeve of the inserter to pivot the suture anchor in the manner illustrated schematically in FIG. 5. Of course, the suture anchor 58a may be inserted into either hard or soft body tissue in a manner which is different than the manner illustrated schematically in FIGS. 4 and 5 using an inserter assembly having a different construction than the inserter assembly 80.

Molded Suture Anchor

Figure 10:
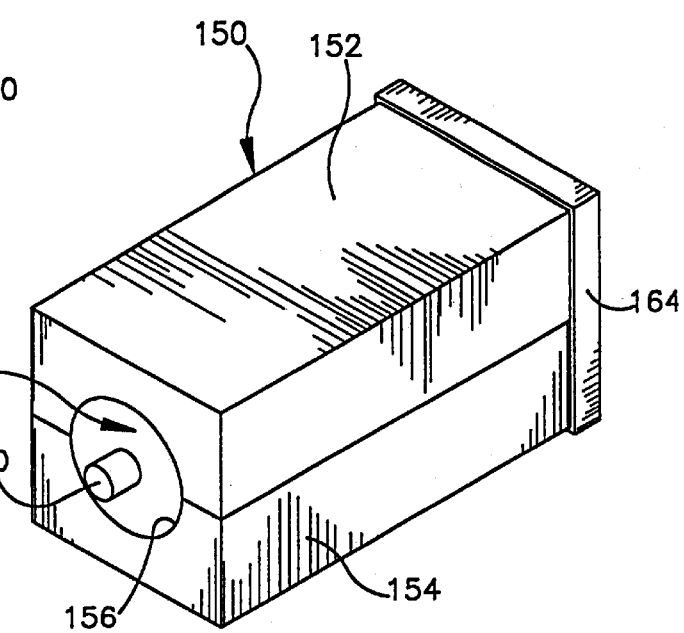
FIG. 10 is a schematic illustration depicting the manner in which a mold is used to shape body tissue to form an anchor.

In the embodiments of the invention illustrated in FIGS. 1–9, the suture anchors 58 and 58a were formed by cutting and/or pressing body tissue. In the embodiment of the invention illustrated in FIG. 10, the suture anchor is formed by molding body tissue. Since the embodiment of the invention illustrated in FIG. 10 is generally similar to the embodiments of the invention illustrated in FIGS. 1–9, similar numerals will be utilized to designate similar components, the suffix letter "b" being associated with the numerals of FIG. 10 to avoid confusion.

When a suture anchor 58b is to be formed, particles of body tissue, such as natural or artificial osseous body tissue, is positioned in a mold 150. The mold 150 includes upper and lower mold sections 152 and 154 which cooperate to define a cylindrical mold chamber 156. The cylindrical mold chamber 156 has a length corresponding to the desired axial extent of the suture anchor 58b. The mold chamber 156 has a diameter which corresponds to the desired diameter of the cylindrical outer side surface of the suture anchor 58b.

A cylindrical thin elongated member or core 160 extends axially through the mold chamber 156. An end plate 164 closes one end of the mold chamber 156 and supports one end of the core 160. A second end plate (not shown) closes the opposite end of the mold chamber 156 and supports the opposite end of the core 160.

Particles of bone and a suitable binder are conducted into the mold chamber. It is believed that it may be preferred to use fibrin as the binder. The natural or artificial bone particles are uniformly coated with the fibrin and completely fill the mold chamber 156. The fibrin is solidified around and interconnects the particles of body tissue to form the suture anchor 58b. It is contemplated that pressure may be applied against the mixture of binder and particles of body tissue in the mold 150 to compact the mixture.

Suture Anchor Formed of Dried Body Tissue

Regardless of which of the various body tissues and methods are utilized to form a suture anchor, it is contemplated that the body tissue may be dried. When a suture anchor formed of dried natural or artificial body tissue is inserted into a patient's body, the suture anchor is exposed to the fluid in the patient's body. The dried tissue of the suture anchor will absorb the fluid in the patient's body.

As the dried suture anchor absorbs the fluids in the patient's body, the suture anchor expands. As the suture anchor expands, it presses against the surrounding tissue of the patient's body and interlocks the suture anchor and the patient's body.

The suture anchor of dried body tissue can be inserted into an opening in a patient's body in the manner illustrated schematically for the suture anchor 58 in FIGS. 4 and 5. The suture anchor of dried body tissue is inserted into the recess 100 and is pivoted in the same manner as previously explained in conjunction with the embodiment of the invention illustrated in FIGS. 4 and 5. Once a suture anchor has been pivoted relative to the patient's body from the orientation shown in FIG. 4 through the orientation shown in FIG. 5 to the orientation shown in FIG. 6, the suture anchor absorbs body fluids and expands to more completely fill the recess 100.

It is contemplated that the suture anchor may be formed of many different types of dried body tissue. Thus, the suture anchor may be formed of dried osseous or bony body tissue. Alternatively, the suture anchor may be formed of dried dense connective body tissue, such as cartilage or tendon tissue. Although hard compact bone tissue may be dried, there will be relatively little expansion of the hard compact bone tissue when it is inserted into the patient's body.

When a suture anchor is formed of dried body tissue, the expansion or swelling of the suture anchor can be used to retain the suture anchor at a location where it would not be retained without expanding or swelling. Thus, a suture anchor formed of dried skin or other soft tissue may be inserted beneath the skin of the patient. The dried skin or other soft tissue forming the suture anchor will immediately begin to absorb the patient's body fluid (blood). As this occurs, the suture anchor will expand. Expansion of the suture anchor beneath the skin of the patient will prevent the suture anchor from being pulled back through the opening through which it was inserted beneath the skin of the patient.

Anchors formed of dried soft body tissue may be used at many different locations in a patient's body. For example, suture anchors formed of dried soft body tissue may be used in association with internal organs. The dried soft body tissue forming a suture anchor may be obtained from any one of many different sources. For example, body tissue may be obtained from inside a human other than the patient or from inside a non-human animal. This body tissue would be sterilized and dried before being formed into a suture anchor.

It is contemplated that the body tissue from which a suture anchor is to be formed may be dried in many different ways. Thus, the body tissue may be freeze dried. When a suture anchor is to be formed, a thin elongated member, corresponding to the thin elongated member 14 of FIG. 1, is inserted into the freeze dried body tissue. The cutting tool 20 is then rotated and moved axially along the thin elongated member to cut the freeze dried body tissue in the same manner illustrated schematically in FIG. 2.

Rather than freeze drying the body tissue, the body tissue could be dried by applying pressure against the body tissue and forcing fluid to flow from the body tissue. Thus, a press, similar to a press disclosed in U.S. Pat. No. 5,329,846 issued Jul. 19, 1994 and entitled "Tissue Press and System" may be utilized to apply pressure against body tissue and force fluid from the body tissue. When the body tissue is dried in this manner, the body tissue may be compressed to a cylindrical configuration with an outside diameter which corresponds to the outside diameter of a suture anchor.

A passage may be formed in the compressed and dried body tissue either before or after it is removed from the press. When the body tissue has been removed from the press, it can be further dried by being exposed to a warm dry environment. Alternatively, the body tissue may be dried without pressing, by exposing the body tissue to a warm dry environment for a sufficient length of time to result in evaporation of the fluid from the body tissue.

Conclusion

The present invention relates to a new and improved suture anchor 58 which is formed of body tissue. The body tissue is shaped to the desired configuration of the anchor 58. The body tissue defines a passage 50 through the anchor 58. A suture 62 is inserted into the passage 50 in the anchor 58. The anchor 58 and the suture 62 are inserted into a patient's body.

The anchor 58 may be formed of many different types of body tissue, including osseous body tissue, bone or dense connective tissue. The body tissue may be dried so that when the anchor 58 is exposed to fluid in a patient's body, the anchor absorbs the fluid and expands. The body tissue may be from the patient's own body, from another human, or from a nonhuman animal.

Having described the invention, the following is claimed:

1. A method of anchoring a suture, said method comprising removing fluid from a piece of dense connective body tissue by compressing the piece of dense connective tissue, forming the piece of dense connective body tissue to have first and second end portions, an outer side surface extending between said first and second end portions, and a passage extending through the piece of dense connective body tissue, inserting a suture into the passage in the piece of dense connective body tissue, and inserting the piece of dense connective body tissue into a patient's body with the first end portion of the piece of dense connective body tissue leading and with the suture extending from the passage in the piece of dense connective body tissue, said step of inserting the piece of dense connective body tissue into the patient's body includes applying force against the second end portion of the piece of dense connective body tissue.

2. A method as set forth in claim 1 wherein said step of forming a piece of dense connective body tissue includes compressing dense connective body tissue to form a sheet having a thickness corresponding to the distance between opposite ends of the piece of dense connective body tissue, cutting a portion from the sheet of dense connective body tissue to at least partially form the outer side surface of the piece of dense connective body tissue, and inserting a thin elongate d member into the dense connective body tissue to at least partially form the passage.

3. A method as set forth in claim 1 wherein said step of forming a piece of dense connective body tissue includes cutting dense connective body tissue of an animal other than a human, said step of inserting the piece of dense connective body tissue into a patient's body includes inserting the piece of dense connective body tissue into a human patient's body.

4. A method as set forth in claim 1 wherein said step of forming a piece of dense connective body tissue includes rotating a cutting tool and moving the cutting tool into dense connective body tissue along a path which extends parallel to an axis about which the cutting tool is rotated to at least partially form the outer side surface of the piece of dense connective body tissue.

5. A method as set forth in claim 1 wherein said step of forming a piece of dense connective body tissue includes rotating a thin elongated member and moving the thin elongated member into dense connective body tissue along a path which extends parallel to an axis about which the thin elongated member is rotated to at least partially form the passage which extends through the piece of dense connective body tissue.

6. A method as set forth in claim 5 wherein said steps of rotating a cutting tool and moving the cutting tool into dense connective body tissue and said steps of rotating a thin elongated member and moving the thin elongated member into dense connective body tissue are performed together.

7. A method as set forth in claim 5 wherein said steps of rotating a cutting tool and moving the cutting tool into dense connective body tissue are performed after performance of said step of rotating a thin elongated member and moving the thin elongated member into the dense connective body tissue.

8. A method as set forth in claim 1 wherein said step of forming a piece of dense connective body tissue includes forming a piece of dense connective body tissue which is at least partially dried, said step of inserting the piece of dense connective body tissue into a patient's body includes positioning the piece of dense connective body tissue in the patient's body at a location where the piece of dense connective body tissue is exposed to body fluid to enable the piece of dense connective body tissue to absorb body fluid.

9. A method as set forth in claim 1 wherein said step of forming a piece of dense connective body tissue includes removing cartilage from the patient's body.

10. A method as set forth in claim 1 wherein said step of forming a piece of dense connective body tissue includes removing at least a portion of the tendon from the patient's body.

11. A method as set forth in claim 1 wherein said step of forming a piece of dense connective body tissue includes placing the dense connective body tissue in a press, and operating the press to apply pressure against the dense connective body tissue in the press to shape the dense connective body tissue in the press during operation of the press.

12. A method as set forth in claim 11 wherein said step of forming a piece of dense connective body tissue further includes cutting the dense connective body tissue shaped by operation of the press to at least partially form the passage.

13. A method as set forth in claim 11 wherein said step of forming a piece of dense connective body tissue further includes cutting the dense connective body tissue shaped by operation of the press to further shape the piece of dense connective body tissue.

14. A method as set forth in claim 1 wherein said step of forming a piece of dense connective body tissue to have a passage includes piercing dense connective body tissue to at least partially form the passage.

15. A method as set forth in claim 1 wherein said step of forming a piece of dense connective body tissue to have an outer side surface includes moving a cutting tool along a linear path to cut dense connective body tissue and at least partially form the outer side surface of the piece of dense connective body tissue.

16. A method as set forth in claim 15 wherein said step of forming a piece of dense connective body tissue further includes piercing dense connective body tissue to at least partially form the passage.

17. A method of anchoring a suture, said method comprising forming a piece of dried body tissue to have a passage extending through the piece of dried body tissue, inserting a suture into the passage in the piece of dried body tissue, and inserting the piece of dried body tissue into a patient's body at a location where the piece of dried body tissue is exposed to fluid in the patient's body to enable the piece of dried body tissue to expand by absorbing fluid from the patient's body wherein said step of forming the piece of dried body tissue includes compressing body tissue to remove fluid from the body tissue.

18. A method as set forth in claim 17 wherein said step of forming a piece of dried body tissue includes compressing body tissue to form a sheet having a thickness corresponding to the distance between opposite ends of the piece of dried body tissue, cutting a portion from the sheet of dried body tissue to at least partially form an outer side surface of the piece of dried body tissue, and inserting a thin elongated member into the dried body tissue to at least partially form the passage.

19. A method as set forth in claim 17 wherein said step of forming a piece of dried body tissue includes cutting body tissue of an animal other than a human, said step of inserting the piece of dried body tissue into a patient's body includes inserting the dried piece of body tissue into a human patient's body.

20. A method as set forth in claim 17 wherein said step of forming a piece of dried body tissue includes rotating a cutting tool and moving the cutting tool into dried body tissue along a path which extends parallel to an axis about which the cutting tool is rotated to at least partially form an outer side surface of the piece of dried body tissue.

21. A method as set forth in claim 20 wherein said step of forming a piece of dried body tissue includes rotating a thin elongated member and moving the thin elongated member along a path which extends parallel to an axis about which the thin elongated member is rotated to at least partially form the passage which extends through the piece of dried body tissue.

22. A method as set forth in claim 21 wherein said steps of rotating a cutting tool and moving the cutting tool into the dried body tissue and said steps of rotating a thin elongated member and moving the thin elongated member into dried body tissue are performed together.

23. A method as set forth in claim 17 wherein said step of forming a piece of dried body tissue includes removing tissue from the patient's body and drying the tissue removed from the patient's body.

24. A method as set forth in claim 23 wherein said step of removing tissue from the patient's body includes removing skin from the patient's body.

25. A method as set forth in claim 17 wherein said step of forming a piece of dried body tissue includes placing body tissue in a press, and operating the press to apply pressure against the body tissue in the press during operation of the press.

26. A method as set forth in claim 17 wherein said step of forming a piece of dried body tissue includes moving a cutting tool along a linear path to cut dried body tissue and at least partially form an outer side surface of the piece of dried body tissue.

27. A method as set forth in claim 26 wherein said step of forming a piece of dried body tissue further includes piercing dried body tissue to at least partially form the passage.

28. A method of anchoring a suture, said method comprising forming a piece of dried material to have a passage extending through the piece of dried material, inserting a suture into the passage in the piece of dried material, and inserting the piece of dried material into a patient's body at a location where the piece of dried material is exposed to fluid in the patient's body to enable the piece of dried material to expand by absorbing fluid from the patient's body wherein said step of forming the piece of dried material includes compressing material to remove fluid from the material.

29. A method as set forth in claim 28 wherein said step of forming a piece of dried material includes compressing material to form a sheet having a thickness corresponding to the distance between opposite ends of the piece of dried material, cutting a portion from the sheet of dried material to at least partially form an outer side surface of the piece of dried material, and inserting a thin elongated member into the dried body tissue to at least partially form the passage.

30. A method as set forth in claim 28 wherein said step of forming a piece of dried material includes rotating a cutting tool and moving the cutting tool into dried material along a path which extends parallel to an axis about which the cutting tool is rotated to at least partially form an outer side surface of the piece of dried material.

31. A method as set forth in claim 30 wherein said step of forming a piece of dried material includes rotating a thin elongated member and moving the thin elongated member along a path which extends parallel to an axis about which the thin elongated member is rotated to at least partially form the passage which extends through the piece of dried material.

32. A method as set forth in claim 31 wherein said steps of rotating a cutting tool and moving the cutting tool into the dried material and said steps of rotating a thin elongated member and moving the thin elongated member into dried material are performed together.

33. A method of anchoring a suture, said method comprising compressing a piece of body tissue to remove fluid from the piece of body tissue, forming an anchor of the piece of body tissue which is capable of absorbing fluid, said step of forming an anchor of the piece of body tissue capable of absorbing fluid includes forming the anchor with a passage which extends through the anchor, inserting a suture into the passage in the anchor, inserting the anchor into a patient's body at a location where the anchor is exposed to fluid in the patient's body, and expanding the anchor under the influence of fluid absorbed from the patient's body to retain the anchor against movement relative to the patient's body.

34. A method of anchoring a suture, said method comprising forming a piece of connective body tissue to have first and second end portions, an outer side surface extending between said first and second end portions, and a passage extending through the piece of connective body tissue, said step of forming a piece of connective body tissue includes at least partially drying the connective body tissue, inserting a suture into the passage in the piece of dried connective body tissue, and inserting the dried piece of connective body tissue into a patient's body with the suture extending from the passage in the dried piece of connective body tissue, said step of inserting the dried piece of connective body tissue into the patient's body includes positioning the dried piece of connective body tissue in the patient's body at a location where the dried piece of connective body tissue is exposed to body fluid to enable the dried piece of connective body tissue to absorb body fluid wherein said step of forming the piece of connective body tissue includes compressing the piece of connective body tissue, and said step of drying the piece of connective body tissue includes removing liquid from the piece of connective body tissue while compressing the piece of connective body tissue.

35. A method as set forth in claim 34 wherein said step of forming a piece of connective body tissue includes cutting connective body tissue of an animal other than a human, said step of inserting the dried piece of connective body tissue into a patient's body includes inserting the piece of dried connective body tissue into a human patient's body.

36. A method as set forth in claim 34 wherein said step of forming a piece of connective body tissue includes rotating a cutting tool and moving the cutting tool into connective body tissue along a path which extends parallel to an axis about which the cutting tool is rotated to at least partially form the outer side surface of the piece of connective body tissue, said step of moving the cutting tool into connective body tissue being performed after having performed said step of drying the connective body tissue.

37. A method as set forth in claim 36 wherein said step of forming a piece of connective body tissue includes rotating a thin elongated member and moving the thin elongated member into connective body tissue along a path which extends parallel to an axis about which the thin elongated member is rotated to at least partially form the passage which extends through the piece of connective body tissue, said step of moving the thin elongated member into connective body tissue being performed after having performed said step of drying the connective body tissue.

38. A method as set forth in claim 37 wherein said steps of rotating a cutting tool and moving the cutting tool into connective body tissue and said steps of rotating a thin elongated member and moving the thin elongated member into connective body tissue are performed together.

39. A method as set forth in claim 37 wherein said steps of rotating a cutting tool and moving the cutting tool into connective body tissue are performed after performance of said step of rotating a thin elongated member and moving the thin elongated member into the connective body tissue.

40. A method as set forth in claim 34 wherein said step of forming a piece of connective body tissue includes removing cartilage from a body.

41. A method as set forth in claim 34 wherein said step of forming a piece of connective body tissue includes removing at least a portion of a tendon from a body.

42. A method as set forth in claim 34 wherein said step of forming a piece of connective body tissue includes placing the connective body tissue in a press, and operating the press to apply pressure against the connective body tissue in the press to shape the connective body tissue in the press during operation of the press, said step of at least partially drying the connective body tissue is performed while performing said step of operating the press.

43. A method as set forth in claim 42 wherein said step of forming a piece of connective body tissue further includes cutting the connective body tissue shaped by operation of the press to at least partially form the passage.

44. A method as set forth in claim 42 wherein said step of forming a piece of connective body tissue further includes cutting the connective body tissue shaped by operation of the press to further shape the piece of connective body tissue.

45. A method as set forth in claim 34 wherein said step of forming a piece of connective body tissue to have a passage includes piercing connective body tissue to at least partially form the passage.

46. A method of anchoring a suture, said method comprising forming a piece of body tissue to have a passage extending through the piece of body tissue, said step of forming a piece of body tissue includes removing liquid from the body tissue, inserting a suture into the passage in the piece of body tissue, and thereafter, inserting the piece of body tissue into a patient's body with the suture extending from the passage in the piece of body tissue, said step of inserting the piece of body tissue into the patient's body includes positioning the piece of body tissue in the patient's body at a location where the piece of body tissue is exposed to body liquid to enable the piece of body tissue to absorb body liquid wherein said step of forming the piece of body tissue includes compressing the piece of body tissue, said step of removing liquid from the piece of body tissue is performed while compressing the piece of body tissue.

47. A method as set forth in claim 46 wherein said step of forming a piece of body tissue includes cutting connective body tissue of an animal other than a human, said step of inserting the piece of body tissue into a patient's body includes inserting the piece of connective body tissue into a human patient's body.

48. A method as set forth in claim 46 wherein said step of forming a piece of body tissue includes rotating a cutting tool and moving the cutting tool into body tissue along a path which extends parallel to an axis about which the cutting tool is rotated, said step of moving the cutting tool into body tissue being performed after having performed said step of removing liquid from the body tissue.

49. A method as set forth in claim 48 wherein said step of forming a piece of body tissue includes rotating a thin elongated member and moving the thin elongated member into body tissue along a path which extends parallel to an axis about which the thin elongated member is rotated to at least partially form the passage which extends through the piece of body tissue, said step of moving the thin elongated member into body tissue being performed after having performed said step of removing liquid from the body tissue.

50. A method as set forth in claim 49 wherein said steps of rotating a cutting tool and moving the cutting tool into body tissue and said steps of rotating a thin elongated member and moving the thin elongated member into body tissue are performed together.

51. A method as set forth in claim 49 wherein said steps of rotating a cutting tool and moving the cutting tool into body tissue are performed after performance of said step of rotating a thin elongated member and moving the think elongated member into the body tissue.

52. A method as set forth in claim 46 wherein said step of forming a piece of body tissue includes removing cartilage from a body.

53. A method as set forth in claim 46 wherein said step of forming a piece of body tissue includes removing at least a portion of a tendon from a body.

54. A method as set forth in claim 46 wherein said step of forming a piece of body tissue includes placing the body tissue in a press, and operating the press to apply pressure against the body tissue in the press to shape the body tissue in the press during operation of the press, said step of removing liquid from the body tissue is at least partially performed while performing said step of operating the press.

55. A method as set forth in claim 54 wherein said step of forming a piece of body tissue further includes cutting the body tissue shaped by operation of the press to at least partially form the passage.

56. A method as set forth in claim 54 wherein said step of forming a piece of body tissue further includes cutting the body tissue shaped by operation of the press to further shape the piece of body tissue.

57. A method as set forth in claim 46 wherein said step of forming a piece of body tissue to have a passage includes piercing body tissue to at least partially form the passage.

58. A method as set forth in claim 46 wherein said step of inserting the piece of body tissue into the patient's body includes moving the piece of body tissue into the patient's body with the piece of body tissue in a first orientation, and applying force against the piece of body tissue to pivot the piece of body tissue from the first orientation to a second orientation while the piece of body tissue is in the patient's body.

59. A method as set forth in claim 58 wherein said step of applying force against the piece of body tissue to pivot the piece of body tissue includes tensioning the suture.

* * * * *